(12) United States Patent
Shinohara et al.

(10) Patent No.: US 9,997,714 B2
(45) Date of Patent: Jun. 12, 2018

(54) HOLE TRANSPORT MATERIAL

(71) Applicant: MERCK PATENT GMBH, Darmstadt (DE)

(72) Inventors: Hiromi Shinohara, Kanagawa Pref. (JP); Atsushi Sawada, Kanagawa Pref. (JP); Elvira Montenegro, Weinheim (DE); Heinrich Becker, Ober-Ramstadt (DE)

(73) Assignee: MERCK PATENT GMBH, Darmstadt (DE)

(*) Notice: Subject to any disclaimer, the term of this patent is extended or adjusted under 35 U.S.C. 154(b) by 258 days.

(21) Appl. No.: 15/026,776

(22) PCT Filed: Sep. 16, 2014

(86) PCT No.: PCT/EP2014/002494
§ 371 (c)(1),
(2) Date: Apr. 1, 2016

(87) PCT Pub. No.: WO2015/049031
PCT Pub. Date: Apr. 9, 2015

(65) Prior Publication Data
US 2016/0254449 A1 Sep. 1, 2016

(30) Foreign Application Priority Data
Oct. 2, 2013 (EP) .................................... 13004770

(51) Int. Cl.
*H01L 51/00* (2006.01)
*H01G 9/20* (2006.01)
(Continued)

(52) U.S. Cl.
CPC .......... *H01L 51/006* (2013.01); *C07C 213/02* (2013.01); *C07C 217/92* (2013.01);
(Continued)

(58) Field of Classification Search
CPC . H01L 51/006; H01L 51/0056; H01G 9/2059; H01G 9/2031; C07C 213/02; C07C 217/92; C07C 2603/97; Y02E 10/542
See application file for complete search history.

(56) References Cited

U.S. PATENT DOCUMENTS 7,540,978 B2 * 6/2009 Pfeiffer .................. C09K 11/06
 136/263
8,304,095 B2 11/2012 Heil et al.
2008/0272693 A1 11/2008 Heil et al.

FOREIGN PATENT DOCUMENTS

CN 101326261 A 12/2008
JP 2011258328 A 12/2011

OTHER PUBLICATIONS

Aksenov et al. "Direct metalfree synthesis of diarylamines from 2-nitropropane via the twofold C-H functionalization of arenes" RSC Adv., 2015, 5, 84849 (Year: 2015).*
(Continued)

*Primary Examiner* — Peter F Godenschwager
*Assistant Examiner* — Andrew J. Oyer
(74) *Attorney, Agent, or Firm* — Millen, White, Zelano and Branigan, P.C.

(57) ABSTRACT

The invention relates to 2,2',7,7'-tetrakis-(N,N'-di-4-methoxy-3-methylphenylamine)-9,9'-spirofluorene, to a process for its preparation, and to its use as hole transport material for electronic or optoelectronic devices, especially for solid-state dye-sensitized solar cells.

16 Claims, 1 Drawing Sheet

(51) Int. Cl.
C07C 213/02 (2006.01)
C07C 217/92 (2006.01)

(52) U.S. Cl.
CPC ......... *H01G 9/2031* (2013.01); *H01G 9/2059* (2013.01); *C07C 2603/97* (2017.05); *H01L 51/0056* (2013.01); *Y02E 10/542* (2013.01)

(56) References Cited

OTHER PUBLICATIONS

Office Action for related Chinese Patent Application No. 201480054535 dated Mar. 3, 2017.
Kuwano, R. et al, "Palladium-Catalyzed N-Arylation of Bis(ortho-substituted aryl)amines: an Efficient Method for Preparing Sterically Congested Triarylamines," SynLett, 2010, No. 12, pp. 1819-1824.
International Search Report for PCT/EP2014/002494 dated Dec. 16, 2014.
Blais, J. M. et al, "Accumulation of persistent organochlorine compounds in mountains of western Canada," Nature, Oct. 8, 1998, vol. 395, pp. 585-588.
English Abstract of JP2011258328, Publication Date: Dec. 22, 2011.

\* cited by examiner

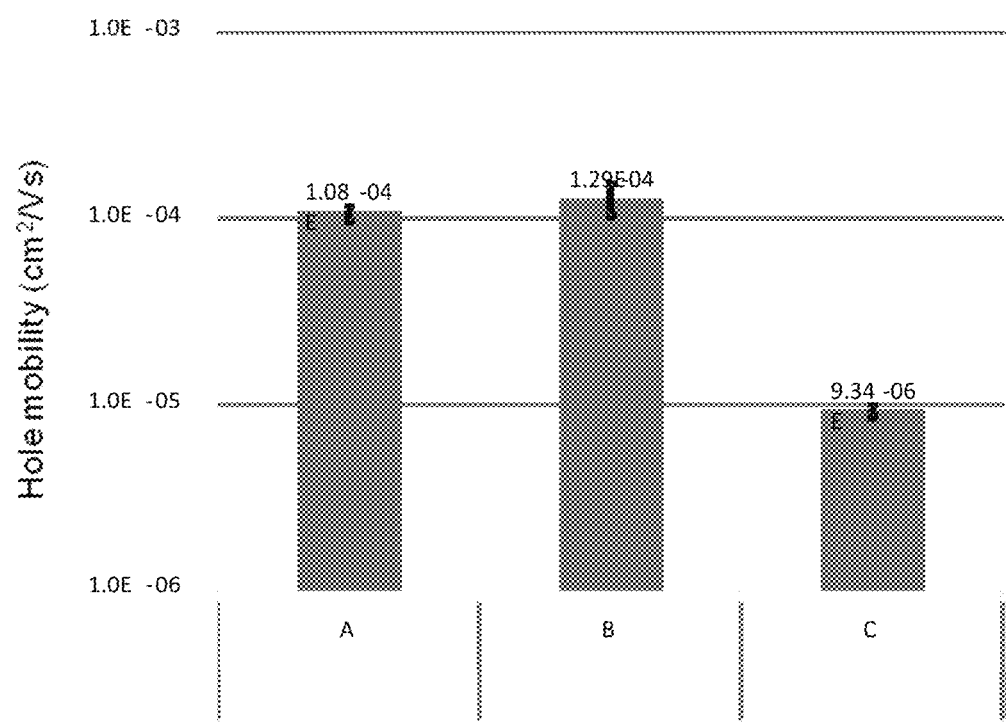

HOLE TRANSPORT MATERIAL

HOLE TRANSPORT MATERIAL

The invention relates to 2,2',7,7'-tetrakis-(N,N'-di-4-methoxy-3-methylphenylamine)-9,9'-spirofluorene, to a process for its preparation, and to its use as hole transport material for electronic or optoelectronic devices, especially for solid-state dye-sensitized solar cells or perovskite containing solar cells.

The use of dye-sensitized solar cells or perovskite containing solar cells is a promising technology to generate photocurrent through the irradiation of solar light. Liquid electrolyte dye-sensitized solar cells reach power conversion efficiencies of over 11%. However, one of the existing tasks for liquid electrolyte based solar cells is to avoid leakage problems. As a consequence, researchers replaced the liquid electrolyte with solid hole-conductors or with other words hole transport materials (HTMs). Up to now, the hole transport material 2,2',7,7'-tetrakis-(N,N'-di-4-methoxyphenylamine)-9,9'-spirobifluorene (spiro-OMeTAD) is selected for the benchmark HTM for solid-state dye sensitized solar cells (sDSSC) (Nature, 1998, 395, 585). However, spiro-OMeTAD has a relatively low charge carrier mobility of the order of $10^{-4}$ cm$^2$/Vs.

Beside of spiro-OMeTAD, further hole transport materials are described in JP 2011-258328, especially compound 39 being 2,2',7,7'-tetrakis-(N,N'-di-4-methoxy-3,5-dimethylphenylamine)-9,9'-spirofluorene.

In addition, one important issue to be solved is the solubility of the HTM because the HTM has to be processable from solution, should fill the pores of the semiconductor efficiently and should form smooth films.

Accordingly, there continues to be a demand for hole transport materials for further optimizing the performance of electronic or optoelectronic devices, especially for optimizing sDSSCs.

Accordingly, the present invention is concerned with the problem of providing an alternative hole transport material having improved properties to be incorporated into electronic or optoelectronic devices.

Surprisingly, it has been found that the compound of formula (I) being 2,2',7,7'-tetrakis-(N,N'-di-4-methoxy-3-methylphenylamine)-9,9'-spirofluorene is a hole transport material having the desired property profile.

The invention therefore relates to the compound of formula (I)

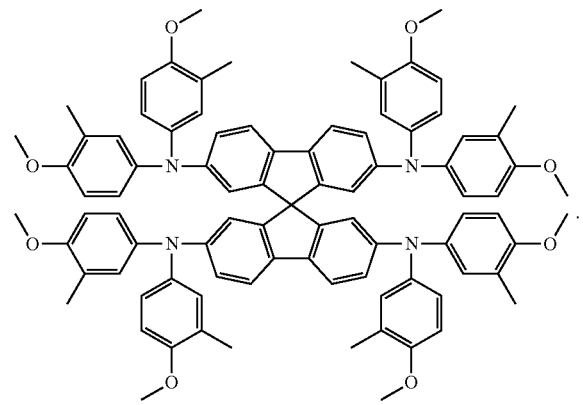

(I)

This hole transport material has better solubility compared to the prior art molecules spiro-OMeTAD and 2,2',7,7'-tetrakis-(N,N'-di-4-methoxy-3,5-dimethylphenylamine)-9,9'-spirofluorene. It is surprising that the solubility is better than spiro-OMeTAD although eight non-polar methyl groups are incorporated into the structure to result in the compound of formula (I). The inventive hole transport material has a better hole mobility than both reference materials.

Thus, the cell performance of a solid state DSSC comprising the compound of formula (I) as described in the experimental section is better than the performance of the sDSSC of the reference substance 2,2',7,7'-tetrakis-(N,N'-di-4-methoxy-3,5-dimethylphenylamine)-9,9'-spirofluorene and equal to the performance of the sDSSC comprising spiro-OMeTAD.

The invention further relates to the process for the preparation of the compound of formula (I) comprising reacting 2,2',7,7'-tetrabromo-9,9'-spirobifluorene in a Buchwald-Hartwig amination with bis(4-methoxy-3-methylphenylamine).

The starting material 2,2',7,7'-tetrabromo-9,9'-spirobifluorene is commercially available e.g. from TCI or Sigma-Aldrich.

The invention is furthermore directed to the starting material bis(4-methoxy-3-methylphenylamine).

Bis(4-methoxy-3-methylphenylamine) can be synthesized through reaction of 5-bromo-2-methoxy-1,3-dimethylbenzene with 4-methoxy-3,5-dimethylphenylaniline. The reaction conditions belong to conditions of a Buchwald-Hartwig amination which are well-known in the art.

The invention is furthermore directed to a process for the preparation of bis(4-methoxy-3-methylphenylamine) comprising reacting 5-bromo-2-methoxy-1,3-dimethylbenzene in a Buchwald-Hartwig amination with 4-methoxy-3,5-dimethylphenylaniline.

Preferred reaction conditions for the synthesis of bis(4-methoxy-3-methylphenylamine) are the use of sodium tert-butoxide as a base, Palladium(II)acetate as source for the Palladium(0) in the Pd-catalyst and 1,1'-bis(diphenylphosphino)ferrocene (DPPF) as ligand. The Buchwald-Hartwig reaction preferably takes place in the presence of an organic solvent e.g. toluene, benzene, dioxane, tetrahydrofurane, dimethylformamide or dimethoxyethane. It is preferred to use toluene as solvent. The reaction temperature is typically between room temperature to 120° C.

Furthermore, the process for the synthesis of the compound of formula (I) is also a Buchwald-Hartwig amination. Reaction conditions for a Buchwald-Hartwig amination are well-known in the art. Preferred reaction conditions for the synthesis of the compound of formula (I) are the use of sodium tert-butoxide, Palladium(II)acetate as source for the Palladium(0) in the Pd-catalyst and 2-dicyclohexylphosphino-2',6'-dimethoxybiphenyl (SPhos) as ligand.

SPhos-Pd-complexes exhibit high activity for Buchwald-Hartwig animation involving aryl chlorides or aryl bromides. The Buchwald-Hartwig reaction preferably takes place in the presence of an organic solvent e.g. toluene, benzene, dioxane, tetrahydrofurane, dimethylformamide or dimethoxyethane. It is preferred to use toluene as solvent and the reaction temperature is typically between room temperature to 120° C., preferably at 120° C.

Preferably, all Buchwald-Hartwig amination take place in the presence of a non-reactive gas such as nitrogen ($N_2$).

The compound of formula (I), prepared by the process outlined above, can be purified by a very wide variety of purification methods which are adequately known to the person skilled in the art, for example by chromatography or recrystallisation.

The present invention furthermore relates to a preparation comprising the compound of formula (I) and at least one solvent.

The preparation may include or comprise, essentially consist of or consist of the said necessary or optional constituents. All compounds or components which can be used in the preparations are either known and commercially available or can be synthesised by known processes.

In addition to the compound of formula (I), the preparation here comprise an organic solvent which is suitable for the applying method used. Suitable methods are dipping, dropping, a doctor blade, a spin coat, brush coating, spray painting or a roll coater. These techniques are well-known for a person skilled in the art. Preferred methods are spin-coating or dipping. A particular preferred method is spin-coating. In most cases, the solvent for spin-coating have a high boiling point.

Suitable organic solvents to be used according to the invention are e.g. chlorobenzene, tetrahydrofuran, butylenes oxide, chloroform, cyclohexanone, acetone, alcohols such as methanol or ethanol, dimethylformamide, acetonitrile, dimethoxyethane, hexamethylphosphoric triamide, 1,2-dichlorobenzene or a mixture thereof. A preferred solvent is chlorobenzene.

The invention also relates to a process for the preparation of a preparation of this type, characterised in that the compound of formula (I) is mixed and/or dissolved, with the at least one solvent and optionally further compounds.

Typical molar concentrations of the compound of formula (I) in the preparation range from 0.08 to 0.5 M, preferably from 0.1 to 0.2 M. The particular preferred concentration in the preparation is 0.17 M. For the purpose of the present invention, the molar concentration refer to the concentration at 25° C.

Furthermore, the preparation according to the invention may comprise one or more further hole transport materials.

Suitable further hole transport materials are well-known in the art. Preferred hole transport materials for combination are spiro-OMeTAD, 2,2',7,7'-tetrakis-(N,N'-di-4-methoxy-3,5-dimethylphenylamine)-9,9'-spirofluorene, tris(p-anisyl)amine, N,N,N',N'-tetrakis(4-methoxyphenyl)-1,1'-biphenyl-4,4'diamine, 2,7-bis[N,N-bis(4-methoxy-phenyl)amino]-9,9-spirobifluorene, poly(3-hexylthiophene) (P3HT), poly(3,4-ethylenedioxythiophene)-poly(styrenesulfonate) (PEDOT:PSS), poly[bis(4-phenyl)(2,4,6-trimethylphenyl)amine] (PTAA), NiO and $V_2O_5$.

Furthermore, the preparation according to the invention may comprise at least one lithium salt.

Suitable lithium salts are lithium bis(trifluoromethylsulfonyl)imide, lithium tris(pentafluoroethyl)trifluorophosphate, lithium dicyanamide, lithium methylsulfate, lithium trifluormethanesulfonate, lithium tetracyanoborate, lithium dicyanamide, lithium tricyanomethide, lithium thiocyanate, lithium chloride, lithium bromide, lithium iodide, lithium hexafluorophosphate, lithium tetrafluoroborate, lithium perchlorate, lithium hexafluoroantimonate, lithium hexafluoroarsenate or a combination of two or more. A preferred lithium salt is lithium bis(trifluoromethylsulfonyl)imide.

Preferably, it comprises from 1 mM to 30 mM, preferably from 8 to 15 mM of the lithium salt.

Furthermore, the preparation according to the invention may comprise at least one further additive.

Suitable additives are pyridine compounds such as tert-butylpyridine, imidazoles as disclosed in WO2013/026563, claims 1 to 15 and disclosed on pages 15 to 17 or polymer additives such as poly(4-vinylpyridine) or its copolymer with e.g. vinylstyrene or alkylmethacrylate. A preferred pyridine compound is tert-butylpyridine. Preferably, the preparation comprises from 0.01 M to 0.3 M, preferably from 0.08 to 0.15 M of the additive.

In one preferred embodiment, the molar ratio of the compound of formula (I):lithium salt:pyridine compound as additive is 10:1:10 at room temperature.

A preferred preparation according to the invention is a preparation comprising the compound of formula (I), at least one solvent, a lithium salt and a pyridine compound as described or preferably described before.

The usefulness of a lithium salt is described in Phys. Chem., Chem. Phys, 2013, 15, 1572-2579.

The usefulness of a pyridine compound is described in Sol. Energy Mater. & Solar Cells, 2007, 91, 424-426.

Furthermore, the preparation according to the invention as described above may comprise a p-dopant such as $N(PhBr)_3$ $SbCl_6$ in which Ph means phenyl, $V_2O_5$, F4-TCNQ (tetrafluoro-tetracyanoquinodimethane) as described in Phys. Chem, Chem., Phys, 2012, 14, 11689-11694, HAT-CN (1,4,5,8,9,11-hexaazatriphenylene-hexacarbonitrile) or Co complex salts as described in Chem. Mater., 2013, 25, 2986-2990 or J. Am. Chem. Soc., 2011, 133, 18042.

The compound of formula (I), as described above is a hole transport material and can therefore likewise be employed in an electronic or optoelectronic device.

The invention therefore relates furthermore to the use of the compound of formula (I) in an electronic or optoelectronic device.

The invention therefore furthermore relates to an electronic or optoelectronic device comprising the compound of formula (I).

An electronic device here is taken to mean a device which comprises at least one layer which comprises at least one organic compound. However, the device may also comprise inorganic materials or also layers built up entirely from inorganic materials.

The electronic or optoelectronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), solar cells, organic optical detectors, organic photoreceptors, organic field-quench devices (O-FQDs), light-emitting electrochemical cells (LECs), organic laser diodes (O-lasers), organic plasmon emitting devices (D. M. Koller et al., Nature Photonics 2008, 1-4), electrophotography devices and wave converter.

The compound of formula (I) is e.g. part of the wave conversion layer of the wave converter.

The electronic device is preferably an organic electroluminescent device (OLED) or an organic light-emitting electrochemical cell (OLEC).

The optoelectronic device is preferably a solid state dye-sensitized solar cell or a perovskite containing solar cell. The optoelectronic device is especially preferably a solid state dye-sensitized solar cell.

The device is furthermore characterized in that the compound of formula (I) is employed as hole transport material.

The invention furthermore relates to a charge transport layer comprising a compound of formula (I).

The charge transport layer according to the invention may comprise the above mentioned additives or further HTMs as described before.

The charge transport layer according to the invention may comprise organic binder, preferably polymeric binder.

Suitable binder to be used according to the invention are polyethylene oxide (PEO), polyvinylidene fluoride (PVDF), polycarbonate, polyacrylate, polymethyl acrylate, polymethylmethacrylate, polystyrene, polyvinyl chloride or polysiloxanes.

The charge transport layer according to the invention is preferably a photosensitized nanoparticle layer comprising a sensitizing dye or a perovskite and the compound of formula (I).

There are no restrictions per se with respect to the choice of the sensitizing dye as long as the LUMO energy state is marginally above the conduction bandedge of the photoelectrode to be sensitized. Examples of dyes are disclosed in Nanoenergy, de Souza, Flavio Leandro, Leite, Edson Roberto (Eds.), Springer, ISBN 978-3-642-31736-1, pages 58 to 74 or black dyes as described in U.S. Pat. No. 8,383,553.

Preferred dyes are organic dyes such as CYC-B11 as described in J. Power Sources, 2012, 214, 113-118, MK-1, MK-2 or MK-3 (its structures are described in FIG. 1 of N. Koumura et al, J. Am. Chem. Soc. Vol 128, no. 44, 2006, 14256-14257), D29 as described on page 4 of WO 2012/001033, D35 as described on page 4 of WO 2012/001033, D102 (CAS no. 652145-28-3), D-149 (CAS no. 786643-20-7), D205 (CAS no. 936336-21-9), D358 (CAS no. 1207638-53-6), YD-2 as described in T. Bessho et al, Angew. Chem. Int. Ed. Vol 49, 37, 6646-6649, 2010, Y123 (CAS no. 1312465-92-1), bipyridin-Ruthenium dyes such as N3 (CAS no. 141460-19-7), N719 (CAS no. 207347-46-4), Z907 (CAS no. 502693-09-6), C101 (CAS no. 1048964-93-7), C106 (CAS no. 1152310-69-4), K19 (CAS no. 847665-45-6), HRS-1 (CAS no. 906061-30-1 as disclosed in K. J. Jiang et al, Chem. Comm. 2460, 2006) or terpyridine-Ruthenium dyes such as N749 (CAS no. 359415-47-7).

The structure of D205 is

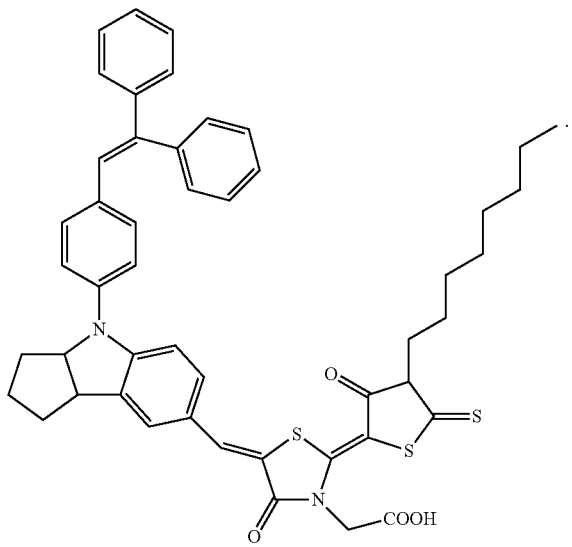 [SMILES: CCCCCCCCC1C(=O)/C(=c2\s/c(=C\c3ccc4c(c3)C3CCCC3N4c3ccc(C=C(c4ccccc4)c4ccccc4)cc3)c(=O)n2CC(=O)O)SC1=S]

The structure of D358 is

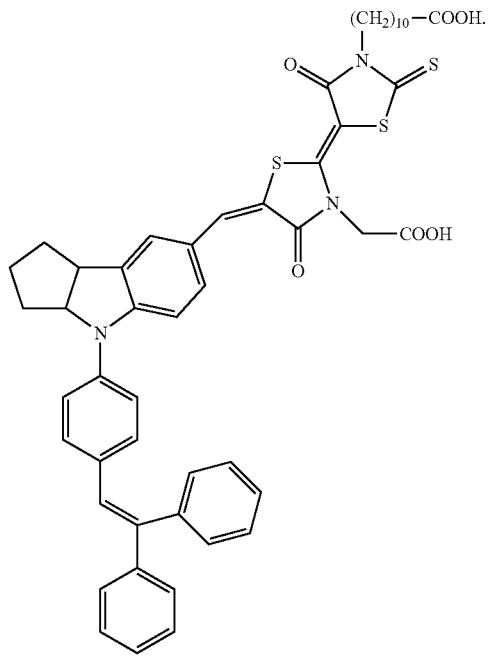

Particularly preferred dyes are Z907 or Z907Na which are both an amphiphilic ruthenium sensitizer, D29, D35, Y123, C106, D358 or HRS-1. The dye Z907Na means NaRu(2,2'-bipyridine-4-carboxylic acid-4'-carboxylate)(4,4'-dinonyl-2,2'-bipyridine)(NCS)$_2$.

A very particular dye is Z907.

There are no restrictions per se with respect to the choice of the perovskite material. Perovskite materials are known to act as light absorbing moiety but they are also described functionally acting as hole transport material or semiconductor.

As a consequence, the perovskite material comprised in the devices according to the invention may be part of the charge transport layer but may also be part of another layer or scaffold within the device.

Suitable pervoskite materials are $CsSnI_3$, $CH_3NH_3PbI_2Cl$, $CH_3NH_3PbI_3$, $CH_3NH_3Pb(I_{1-x}Br_x)_3$, $CH_3NH_3SnI_2Cl$, $CH_3NH_3SnI_3$ or $CH_3NH_3Sn(I_{1-x}Br_x)_3$ wherein x is each independently defined as follows: (0<x≤1). More generalizing, suitable perovskite materials may comprise two halides corresponding to formula $Xa_{(3-x)}Xb_{(x)}$, wherein Xa and Xb are each independently selected from Cl, Br, or I, and x is greater than 0 and less than 3.

Suitable pervoskite materials are also disclosed in WO 2013/171517, claims 52 to 71 and claims 72 to 79, which is entirely incorporated herein by reference. The materials are defined as mixed-anion perovskites comprising two or more different anions selected from halide anions and chalcogenide anions. Preferred perovskite materials are disclosed on page 18, lines 5 to 17. As described, the perovskite is usually selected from $CH_3NH_3PbBrI_2$, $CH_3NH_3PbBrCl_2$, $CH_3NH_3PbIBr_2$, $CH_3NH_3PbICl_2$, $CH_3NH_3SnF_2Br$, $CH_3NH_3SnF_2I$ and $(H_2N=CH-NH_2)PbI_{3z}Br_{3(1-z)}$, wherein z is greater than 0 and less than 1.

The charge transport layer according to the invention as described before or the device according to the invention as described before or below may furthermore comprise an insulator such as alumina as described in Michael M. Lee et al, Science, 338, 643, 2012.

The charge transport layer according to the invention or the device according to the invention as described before or below may furthermore comprise semiconductor oxide nanoparticles. The charge transport layer according to the invention or the device according to the invention preferably comprises semiconductor oxide nanoparticles.

According to a preferred embodiment of the invention, the semiconductor is based on material selected from the group of Si, $TiO_2$, $SnO_2$, $Fe_2O_3$, $WO_3$, ZnO, $Nb_2O_5$, CdS, ZnS, PbS, $Bi_2S_3$, CdSe, GaP, InP, GaAs, CdTe, $CuInS_2$, and/or $CuInSe_2$. Preferably, the semiconductor comprises a mesoporous surface, thus increasing the surface optionally covered by the sensitizing dye or perovskite material and being in contact with the hole transport material. Preferably, the semiconductor oxide nanoparticles are titanium dioxide nanoparticles. Preferably, the semiconductor oxide is mesoporous.

Preferably, the charge transport layer according to the invention as described before is present on a glass support or plastic or metal foil, optionally together with a dense layer of $TiO_2$. Preferably, the support is conductive.

The present invention furthermore relates to a electronic device or optoelectronic device comprising a charge transport layer as described or preferably described before. Preferably, the invention relates furthermore to a solid-state dye-sensitized solar cell comprising a charge transport layer as described or preferably described before.

Suitable device structures according to the invention comprising further a mixed halide perovskite are described in WO 2013/171517, claims 52 to 71 and claims 72 to 79, which is entirely incorporated herein by reference.

Suitable device structures according to the invention comprising further a dielectric scaffold together with perovskite material are described in WO 2013/171518, claims 1 to 90 or WO 2013/171520, claims 1 to 94 which are entirely incorporated herein by reference.

Suitable device structures according to the invention comprising further a semiconductor and a perovskite material are described in WO 2014/020499, claims 1 and 3 to 14, which is entirely incorporated herein by reference The surface-increasing scaffold structure described therein comprises nanoparticles which are applied and/or fixed on a support layer, e.g. porous $TiO_2$.

Suitable device structures according to the invention comprising a planar heterojunction are described in WO 2014/045021, claims 1 to 39, which is entirely incorporated herein by reference. Such a device is characterized in having a thin film of a light-absorbing or light-emitting perovskite disposed between n-type (electron conducting) and p-type (hole-conducting) layers. Preferably, the thin film is a compact thin film.

Additionally, the invention relates to a method of preparing an electrochemical device and/or optoelectronic device as described or preferably described before, the method comprising the steps of:
  providing a first and a second electrode;
  providing a charge transport layer according to the invention as described before.

There are no restrictions per se with respect to the choice of the first and second electrode. The substrate may be rigid or flexible.

A preferred embodiment of the invention is a solid-state dye-sensitized solar cell comprising a glass substrate coated with F-doped $SnO_2$, a dense layer of $TiO_2$, the inventive charge-transport layer as described or preferably described before and a counter electrode.

Preferably, the counter electrode is a gold electrode, a silver electrode or a platinum electrode. Particularly preferably, the counter electrode is a gold or silver electrode.

The invention furthermore relates to a module comprising a device according to the invention as described before or preferably described before.

The invention furthermore relates to a module comprising a plurality of devices according to the invention as described before or preferably described before.

BRIEF DESCRIPTION OF THE DRAWINGS

FIG. 1 represents hole mobility of the invention and reference materials.

The present invention will now be illustrated, without limiting its scope, by way of the following examples. Even without further comments, it is assumed that a person skilled in the art will be able to utilize the above description in the broadest scope. The preferred embodiments and examples should therefore merely be regarded as descriptive disclosure which is absolutely not limiting in any way.

EXAMPLES

Example 1

Synthesis of 2,2',7,7'-tetrakis-(N,N'-di-4-methoxy-3-methylphenylamine)-9,9'-spirobifluorene Step 1: Synthesis of bis(4-methoxy-3-methylphenylamine)

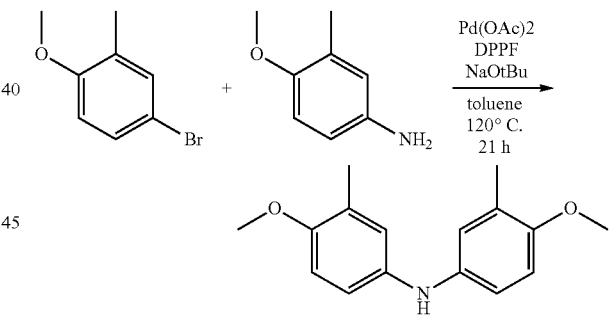

4-Bromo-1-methoxy-2-methylbenzene (3.134 mg, 15.6 mmol), sodium tert-butoxide (3.053 g, 32 mmol), Palladium (II) acetate (69 mg, 0.3 mmol), 1,1'-bis(diphenylphosphino) ferrocene (DPPF) (169 mg, 0.3 mmol) are dissolved in toluene (10 ml) in a 4-neck flask with condenser. The reaction mixture is stirred under $N_2$ flow for 5 minutes, then 4-methoxy-3-methylphenylaniline (2.064 g, 15.0 mmol) and 40 mL of toluene are added. The mixture is heated to 120° C. for 21 h. After the reaction, the reaction mixture is filtered. After concentration by rotary evaporator and purification by flash column chromatography over silica gel (hexane/EtOAc 2%->20%) the product is obtained as an orange viscous oil. This oil is recrystallized by hexane thermally, to obtain bis(4-methoxy-3-methylphenyl)amine as white solid [2.725 g, 10.6 mmol, yield 70.4%)].

$C_{16}H_{19}NO_2$, MW 257.33, Exact MS 257, GC-MS 257 [M]+).

Step 2: Synthesis of 2,2',7,7'-tetrakis-(N,N'-di-4-methoxy-3-methylphenylamine)-9,9'-spirobifluorene

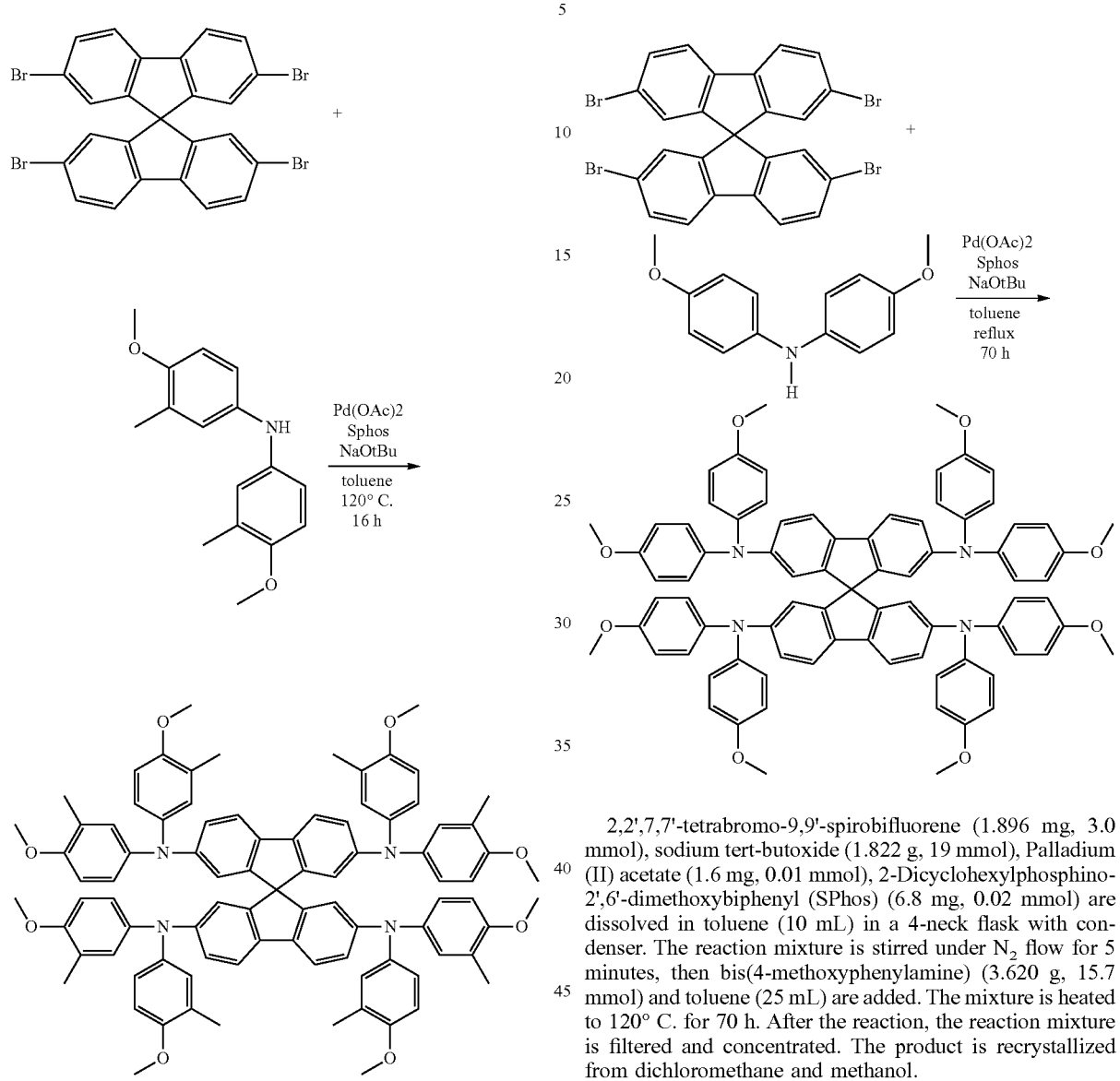

2,2',7,7'-tetrabromo-9,9'-spirobifluorene (639 mg, 1.01 mmol), sodium tert-butoxide (608 g, 6.33 mmol), Palladium (II) acetate (29 mg, 0.13 mmol), 2-Dicyclohexylphosphino-2',6'-dimethoxybiphenyl (SPhos) (41 mg, 0.10 mmol) are dissolved in toluene (10 mL) in a 4-neck flask with condenser. The reaction mixture is stirred under $N_2$ flow for 5 minutes, then bis(4-methoxy-3-methylphenylamine) prepared according to step 1 (1.253 g, 4.87 mmol) and toluene (20 mL) are added. The mixture is heated to 120° C. for 16 h. After the reaction, the reaction mixture is filtered. After concentration by rotary evaporator and purification by flash column chromatography over silica gel (hexane/EtOAc 5%->40%) the product is obtained as a beige amorphous solid [1.082 g, 0.81 mmol, yield 80.0%].

$C_{89}H_{84}N_4O_8$, MW 1337.64, Exact MS 1336, LC-ESI-MS 1337.7 [M+H]+).

Example 2

Synthesis of the reference material spiro-OMeTAD 2,2',7,7'-tetrabromo-9,9'-spirobifluorene (1.896 mg, 3.0 mmol), sodium tert-butoxide (1.822 g, 19 mmol), Palladium (II) acetate (1.6 mg, 0.01 mmol), 2-Dicyclohexylphosphino-2',6'-dimethoxybiphenyl (SPhos) (6.8 mg, 0.02 mmol) are dissolved in toluene (10 mL) in a 4-neck flask with condenser. The reaction mixture is stirred under $N_2$ flow for 5 minutes, then bis(4-methoxyphenylamine) (3.620 g, 15.7 mmol) and toluene (25 mL) are added. The mixture is heated to 120° C. for 70 h. After the reaction, the reaction mixture is filtered and concentrated. The product is recrystallized from dichloromethane and methanol.

Example 3

Synthesis of the reference material 2,2',7,7'-tetrakis-(N,N'-di-4-methoxy-3,6-dimethylphenylamine)-9,9'-spirobifluorene Step 1: Synthesis of bis(4-methoxy-3,6-dimethylphenylamine)

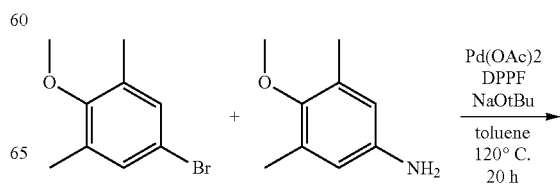

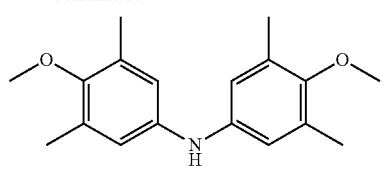

5-Bromo-2-methoxy-1,3-dimethylbenzene (4.179 mg, 21.9 mmol), sodium tert-butoxide (4.468 g, 46.5 mmol), Palladium(II) acetate (93 mg, 0.4 mmol), 1,1'-bis(diphenylphosphino)ferrocene (DPPF) (220 mg, 0.4 mmol) are dissolved in toluene (20 ml) in a 4-neck flask with condenser. The reaction mixture is stirred under $N_2$ flow for 5 minutes, then 4-methoxy-3,5-dimethylphenylaniline (3.032 g, 20.0 mmol) and 60 mL of toluene are added. The mixture is heated to 120° C. for 20 h. After the reaction, the reaction mixture is filtered. After concentration by rotary evaporator and purification by flash column chromatography over silica gel (hexane/EtOAc 2%->20%) the product is obtained as an orange viscous oil. This oil is thermally recrystallized by hexane to obtain bis(4-methoxy-3,5-methylphenyl)amine as white solid [2.961 g, 10.37 mmol, yield 51.7%)].

$C_{18}H_{23}NO_2$, MW 285.38, Exact MS 285, GC-MS 285.1 $[M]^+$ UV max 288 nm.

Step 2: Synthesis of 2,2',7,7'-tetrakis-(N,N'-di-4-methoxy-3,6-dimethylphenylamine)-9,9'-spirobifluorene

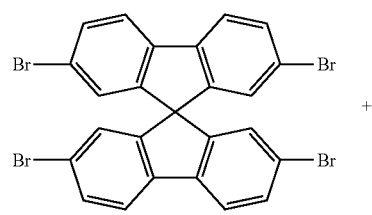

+

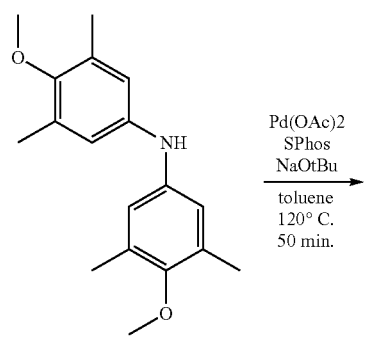

Pd(OAc)2
SPhos
NaOtBu
→
toluene
120° C.
50 min.

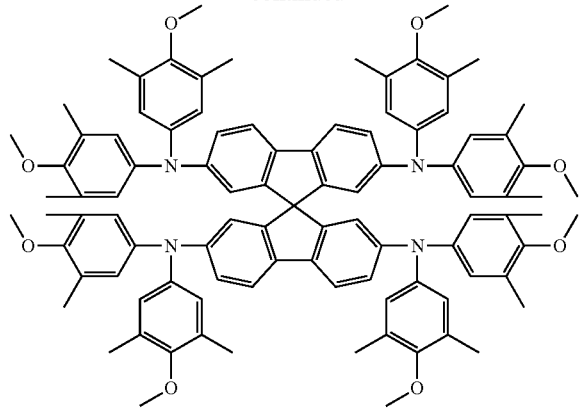

2,2',7,7'-tetrabromo-9,9'-spirobifluorene (316 mg, 0.5 mmol), sodium tert-butoxide (629 g, 6.55 mmol), Palladium (II) acetate (12 mg, 0.05 mmol), 2-Dicyclohexylphosphino-2',6'-dimethoxybiphenyl (SPhos) (22 mg, 0.05 mmol) are dissolved in toluene (5 mL) in a 4-neck flask with condenser. The reaction mixture is stirred under $N_2$ flow for 5 minutes, then bis(4-methoxy-3,5-dimethylphenylamine) (C-1) (316 g, 1.11 mmol) and toluene (25 mL) are added. The mixture is heated to 120° C. for 50 min. After the reaction, the reaction mixture is filtered. After concentration by rotary evaporator and purification by flash column chromatography over silica gel (hexane/EtOAc 5%->80%) the product is obtained as a beige amorphos solid [190 mg, 0.13 mmol, yield 26.6%].

$C_{97}H_{100}N_4O_8$, MW 1449.85, Exact MS 1448, LC-ESI-MS 1449.1 $[M+H]^+$)."

Example A

Solubility of the compounds of Examples 1, 2 and 3

General Description:

A solution for a spin-coat is prepared in a $N_2$ glove box as follows: at first, 20 mg of a hole transport material is dissolved in 95 μL of chlorobenzene. The hole transport material needs to be dissolved completely. A mother solution of lithium bis(trifluorosulfonyl)imide (LiTFSI) and tert-butylpyridine (TBP) is prepared separately at room temperature and is added to the hole transporter solution to set the molar ratio to [hole transporter]:[LiTFSI]:[TBP]=10:1:10 at room temperature. Thus the final volume of the solution is 100 μL.

The solubility of the HTMs according to examples 1, 2 and 3 are evaluated qualitatively:

1 means: 20 mg of HTM is completely dissolved without heating 2 means: HTM is dissolved after heating to 80° C.

3 means: HTM is dissolved after adding salt and base solution and heating to 80° C.

4 means: HTM is dissolved after adding another 50 μL of chlorobenzene and heat to 80° C. (final folume 150 μl).

The result is shown in Table 1:

|  | 1 | 2 | 3 | 4 |
|---|---|---|---|---|
| Example 2 (ref) | — | ✓ |  |  |
| Example 3 (ref.) | — | — | — | ✓ |
| Example 1 | ✓ |  |  |  |

The hole transport material according to the invention has better solubility than the reference materials.

Example B

Using the solution as described in Example A, a solid state dye-sensitized solar cell is fabricated according to Lukas Schmid-Mende and Michael Grätzel, Thin Solid Films, 500, 2006, 296-301.

After cleaning the patterned ITO/ATO substrates (20×20 mm) with Helmanex and water, the TiO$_2$ compact layer is prepared by a sol-gel method using 60 mM TiCl$_4$ aqueous solution at 75° C. for 30 min for three times. A nanocrystalline TiO$_2$ layer is fabricated through screen printing of a TiO$_2$ paste containing 30 nm-sized anatase particles (JGC C&C PST-30NRD) followed by sintering at 500° C. for 30 min. A top TiO$_2$ coat is deposited by sol-gel method using 60 mM TiCl$_4$ aqueous solution at 75° C. for 30 min once and sintered at 500° C. for 30 min. Obtained TiO$_2$ substrates are sensitized by dipping in a 0.3 mM solution of amphiphilic polypyridyl ruthenium complex, cis-RuLL'(SCN)$_2$ (L=4,4'-dicarboxylic acid-2,2'-bipyridine, L'=4,4'-dinonyl-2,2'-bipyridine, Z907) with 0.075 mM of bis-(3,3-dimethyl-butyl)-phosphinic acid (DINHOP) in acetonitrile:tert-butanol (1:1 vol %) and placed in a refrigerator overnight. The hole transport materials are independently coated by spin-coater. 40 μL of the solution is put onto one substrate with waiting time for 30 sec and spinning condition of 2500 rpm for 30 sec. To finish the device fabrication, a 200 nm of Ag electrode is evaporated on top. This procedure results in two cells on one substrate. The measurements for performance are done without sealing he cells.

Current-Voltage characteristics are measured by a source meter (Keithley 2400) under simulated AM 1.5 G sunlight at 100 mW cm$^{-2}$ irradiance, generated using a solar simulator (L11 Peccell Technologies) and calibrated using a calibrated silicon reference cell (Bukou Keiki, BS-520). The solar cells are masked with a metal aperture to define the active area which is typically 0.16 cm$^2$.

The cell structure measured in this experiment and their current-voltage characteristics are summarized in table 2.

TABLE 2

| | current-voltage property of each cell: | | | |
|---|---|---|---|---|
| HTM | $J_{sc}$/mA cm$^{-2}$ | $V_{OC}$/V | FF | PCE/% |
| Example 2 (ref.) | 3.67 | 0.744 | 0.532 | 1.45 |
| Example 3 (ref.) | 1.92 | 0.734 | 0.493 | 0.69 |
| Example 1 | 2.74 | 0.787 | 0.669 | 1.43 |

The result indicates, that the inventive compound of formula (I) has a comparable conversion efficiency with better solubility than spiro-OMeTAD.

Example C

Hole Mobility

The hole mobility of the inventive compound 2,2',7,7'-tetrakis-(N,N'-di-4-methoxy-3-methylphenylamine)-9,9'-spirobifluorene is measured and the value is compared with those of the reference materials according to example 2 and example 3.

The structure of the measurement cell is ITO(200 nm)/PEDOT-PSS(150 nm)/HTM(400 nm)/Au(60 nm).

PEDOT-PSS means poly(3,4-ethylenedioxythiophene)-poly(styrenesulfonate).

The measurement is carried out using four cells for each HTM by means of impedance spectroscopy. (Ref. 1. H. Martens et al., Phys. Rev. B, 60, R8489 (1999), Ref. 2. S. Ishihara, et al., Proc. of IDW'09, p 1085 (2009)). In the impedance measurement, a direct current (dc) voltage is applied to the test cell in order to inject holes from an anode. The hole mobility is determined under the dc field intensity of 10$^5$V/cm. The measurement result is shown in FIG. 1 and in Table 3.

TABLE 3

| | Hole mobility [cm$^2$/Vs] |
|---|---|
| Example 2 (ref) = A | 1.08E-04 |
| Example 3 (ref.) = C | 9.34E-06 |
| Example 1 = B | 1.29E-04 |

The hole mobility of the inventive compound 2,2',7,7'-tetrakis-(N,N'-di-4-methoxy-3-methylphenylamine)-9,9'-spirobifluorene is larger than the hole mobility of spiro-OMeTAD and more than one order of magnitude larger than the hole mobility of the reference example 3. The result of FIG. 1 can well interpret the result of Table 2 in terms of the hole mobility of the used hole transport material.

The invention claimed is:

1. A compound of formula (I)

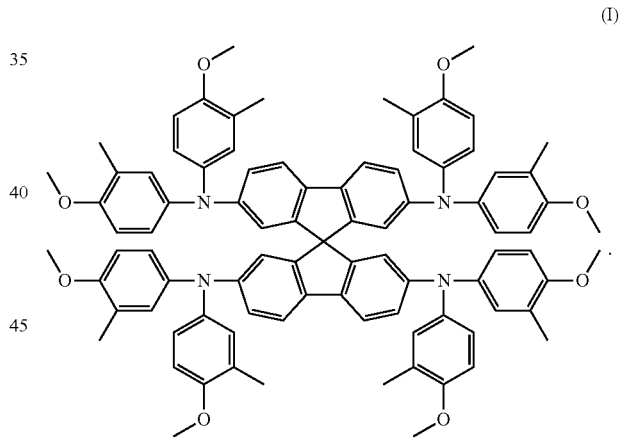

(I)

2. A process for the preparation of the compound according to claim 1 comprising reacting 2,2',7,7'-tetrabromo-9,9'-spirobifluorene in a Buchwald-Hartwig amination with bis(4-methoxy-3-methylphenylamine).

3. A process according to claim 2 in which the reaction is carried out at temperatures between 100° C. and 140° C.

4. Composition comprising the compound of formula (I) according to claim 1 and at least one solvent.

5. Electronic or optoelectronic device comprising the compound of formula (I) according to claim 1.

6. Device according to claim 5 which is an organic electroluminescent device, an organically integrated circuit, an organic field-effect transistor, an organic thin-film transistor, an organic light-emitting transistor, a solar cell, an organic optical detector, an organic photoreceptor, an organic field-quench device, a light-emitting electrochemical cell or an organic laser diode, an organic plasmon emitting device, an electrophotography device or a wave converter.

7. Device according to claim 5 which is a solid-state dye-sensitized solar cell or a perovskite containing solar cell.

8. Device according to claim 5, characterized in that the compound of formula (I) is employed as hole transport material.

9. Charge transport layer comprising a compound of formula (I) according to claim 1.

10. A layer according to claim 9 which is a photosensitized nanoparticle layer comprising a sensitizing dye or perovskite and the compound of formula (I).

11. A layer according to claim 9 further comprising an insulator.

12. A layer according to claim 9 comprising semiconductor oxide nanoparticles.

13. Device according to claim 7 comprising a charge transport layer comprising a compound of formula I.

14. A module comprising a device according to claim 5.

15. The compound bis(4-methoxy-3-methylphenylamine).

16. A process for the preparation of bis(4-methoxy-3-methylphenylamine) comprising reacting 4-Bromo-1-methoxy-2-methylbenzene in a Buchwald-Hartwig amination with 4-methoxy-3-methylphenylaniline.

* * * * *